United States Patent [19]

Guter

[11] Patent Number: 5,061,638

[45] Date of Patent: Oct. 29, 1991

[54] NITRATE ANALYZER

[75] Inventor: Gerald A. Guter, Bakersfield, Calif.

[73] Assignee: Boyle Engineering Corporation, Newport Beach, Calif.

[21] Appl. No.: 395,725

[22] Filed: Aug. 18, 1989

[51] Int. Cl.⁵ .......................................... G01N 30/00
[52] U.S. Cl. ...................................... 436/110; 436/52; 436/114; 436/115; 436/128; 436/161; 210/198.2; 210/635; 210/656
[58] Field of Search ............... 436/110, 128, 129, 161, 436/114, 115, 52; 422/70; 210/198.2, 635, 656

[56] References Cited

U.S. PATENT DOCUMENTS

| | | | |
|---|---|---|---|
| 3,775,088 | 11/1973 | Higgins | 71/1 |
| 3,785,771 | 6/1974 | Luchsinger | 23/230 R |
| 3,920,398 | 11/1975 | Small et al. | 23/230 |
| 4,036,751 | 7/1977 | Orita | 210/35 |
| 4,251,219 | 2/1981 | Larson | 23/230 R |
| 4,314,823 | 2/1982 | Rich, Jr. | 23/230 R |
| 4,334,949 | 6/1982 | Ameen | 756/642 |
| 4,403,039 | 9/1983 | Ban | 436/150 |
| 4,432,878 | 2/1984 | Emshoff | 210/662 |
| 4,434,058 | 2/1984 | Emshoff | 210/662 |
| 4,595,508 | 6/1986 | Wolfe | 210/631 |
| 4,622,133 | 11/1986 | Furano | 210/96.2 |
| 4,671,879 | 6/1987 | Solt | 210/610 |
| 4,681,025 | 8/1987 | Dalgaard | 23/230 R |

OTHER PUBLICATIONS

CA 109(20): 175920w, "Simultaneous Determination of Common Anions by Ion Chromatography", Laboratory Method, No. 9/22.

CA 105(6): 53690t, "Applications of Ion-Exchange Minicolums in a Flow-Injector System for the Spectrophotometric Determination of Anions".

Primary Examiner—David L. Lacey
Assistant Examiner—David Redding
Attorney, Agent, or Firm—Irell & Manella

[57] ABSTRACT

A system and method for determining the concentration of nitrate ions in a nitrate ion-containing water sample which also contains chloride ions and bicarbonate ions is disclosed. The potentially interfacing chloride ions are suppressed by reaction with a cation exchange resin in the silver form. The potentially interferring bicarbonate ions are suppressed by reaction with a cation exchange resin in the hydrogen form. The sample, after having been treated with the two resins is passed into a conductivity cell with the conductivity being directly related to the nitrate ion concentration of the sample. The device and method find advantageous application in automated systems for monitoring and controlling water treatment facilities.

3 Claims, 2 Drawing Sheets

5,061,638

NITRATE ANALYZER

FIELD OF THE INVENTION

This invention relates to an analyzer for determining the nitrate content of water samples. More particularly, it relates to an automated system for repeatedly determining the nitrate content of a water supply thus, in preferred embodiments, to provide information on the effectiveness of water purification systems which remove nitrate ions.

BACKGROUND OF THE INVENTION

There are presently many concerns with the possible adverse health conditions associated with elevated nitrate content of water. Nitrate con enter the water supply from natural sources but also can come from fertilizer use, and the like. The concerns surrounding elevated nitrate levels become with potable water, but are also present with waste waters and the like.

A body of references exist which are directed to methods for the removal of nitrate from water or to the measurement of nitrate in water. U.S. Pat. No. 4,671,879 to Solt et al. describes a method for reducing the nitrate content in water using an ion-exchange resin. U.S. Pat. No. 4,622,133 to Furano describes a dual train system for removing ions such as nitrate from water. U.S. Pat. No. 3,775,088 to Higgins describes another nitrate removal system.

Examples of apparatus for analyzing liquids for their ion content include the system shown in U.S. Pat. No. 3,785,771 to Luchsinger et al. This patent describes a method for removing macromolecules so that they will not interfere with later ion measurements. U.S. Pat. No. 4,681,025 to Dalgaard, describes a system for monitoring pH (hydrogen ion content) in the presence of other potentially interfering ions. This patent shows using cation exchange resins to remove ions which interfere with pH measurement. Another representative reference is U.S. Pat. No. 4,251,219 to Larson et al., which describes a system for measuring low levels of chloride, sulfate, phosphate, nitrate and other ions in a low-pressure condensate. U.S. Pat. No. 4,314,823 to Rich et al., describes a combination conductivity and ion-exchange resin system which allows qualitation and quantitation of a mixture of chlorides, carbonates, acetates, formates, and the like.

The present invention id directed specifically to an analyzer system designed to permit the measurement of nitrate ions in the presence of other contaminating species, particularly chloride and bicarbonate.

STATEMENT OF THE INVENTION

A system and method for determining the concentration of nitrate ions in a nitrate ion-containing water sample which also contains chloride ions and bicarbonate ions has now been developed. In the system or device aspects of this invention it provides a system which includes a sample control valve in series with an analytical train. The sample valve is connected to a source of relatively nitrate, chloride and bicarbonate ion-free carrier water and a source of the sample. The sample control valve is capable of selectively inserting a predetermined volume of the sample into a flow of the carrier water. This sample is then admitted to the analytical train. The analytical train is made up of an initial suppressor column set which includes, in series, a cation-exchange resin column in a silver ion form and a cation-exchange resin column in a hydrogen ion form, the amount of resin in the silver ion form being sufficient to insolubilize the chloride ions present int eh sample on the silver ions, and the amount of the resin in the hydrogen ion form being sufficient to react with the bicarbonate ions present in the sample. This gives rise to a flow of carrier water carrying a chloride ion and bicarbonate ion-free nitrate ion-containing water sample. The next element of the analytical train is a conductivity measuring cell which is positioned to receive the flow of carrier water and the chloride ion and bicarbonate ion-free water sample. The conductivity cell is capable of noting and reporting the change in conductivity which occurs when the nitrate-ion containing sample passes through it. This change in conductivity is a measure of the concentration of nitrate ions present in the sample. In additional aspects, the device can include means for relating the conductivity so measured to the content of nitrate ion present in the sample.

In the process aspects, this invention provides a method for determining the concentration of nitrate ions in aqueous effluent when the effluent additionally contains chloride ions and bicarbonate ions. This method includes the step of (1) admitting a measured volume of the sample to a suppressor column. The suppressor column includes ion-exchange columns containing silver ions and hydrogen ions in sufficient quantity to react with the bicarbonate and chloride ions and remove them from the sample, thereby forming a chloride ion- and bicarbonate ion-free sample;

(2) passing the chloride ion- and bicarbonate ion-free sample into a conductivity cell;

(3) measuring the conductivity of the chloride ion- and bicarbonate ion-free sample; and (4) relating the conductivity so measured to the concentration of nitrate ion in the sample.

In additional aspects of the process, the flow of chloride ion and bicarbonate ion-free carrier water can be continued after the measurement has been carried out so as to equilibrate with the suppressor columns and remove chloride ions and bicarbonate ions, thereby regenerating the suppressor columns for the next sample.

DETAILED DESCRIPTION OF THE INVENTION

Brief Description of the Drawings

This invention will be described with reference being made to the attached drawings in which.

DESCRIPTION OF PREFERRED EMBODIMENTS

Figure 1:
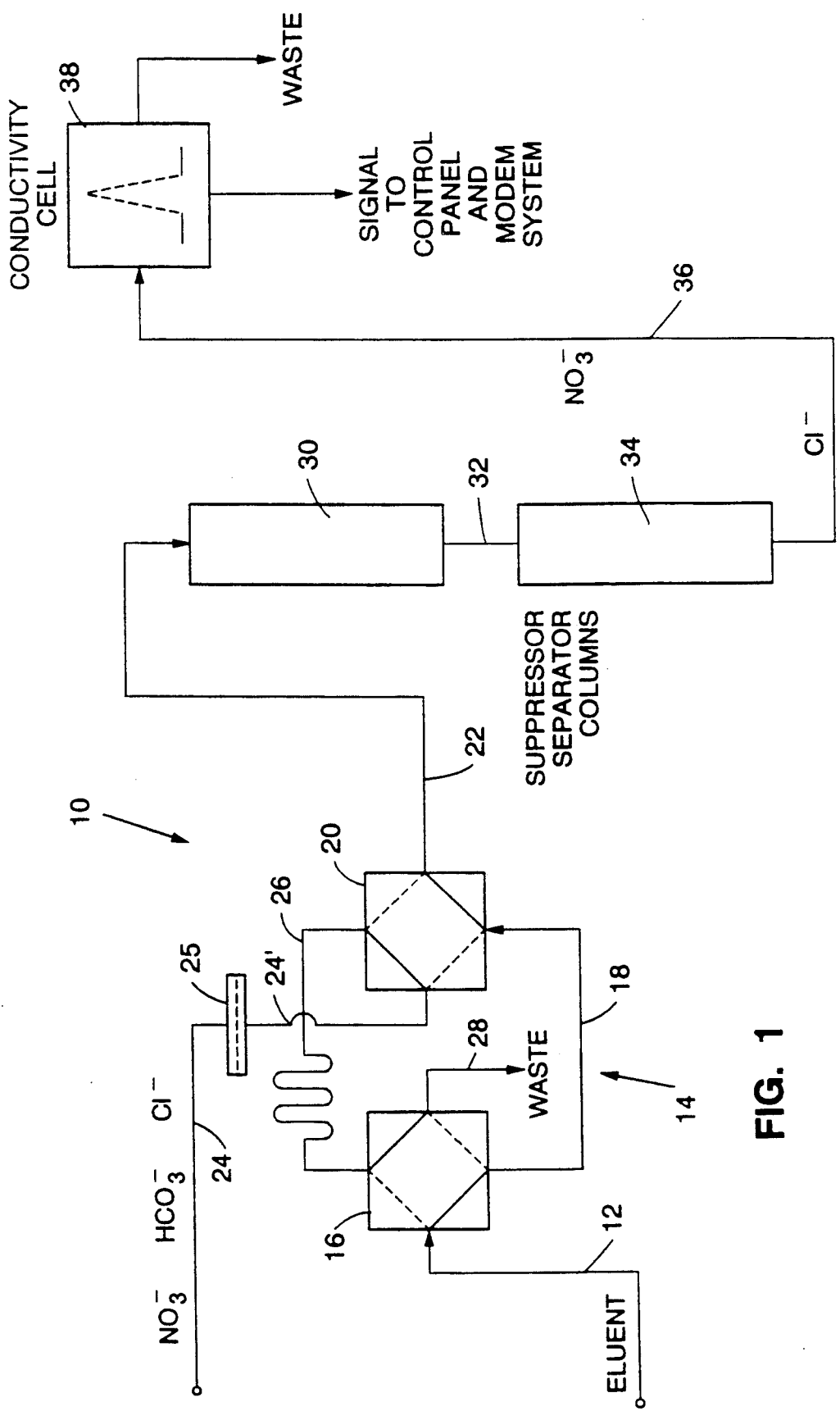
FIG. 1 is a schematic drawing of the analyzer system of this invention and FIG. 2 is a graph illustrating the concentration of nitrate ion observed in a sample as a function of time using the conductivity measuring analyzer system of this invention.

An analyzer 10 is accord with this invention is depicted in FIG. 1. Carrier water (eluant), which should be substantially nitrate ion, chloride ion and bicarbonate ion-free and typically is distilled water, is provided via line 12 to control valve 14. In the embodiment shown, valve 14 is a two stage two position valve. The first stage, 16, in the position shown, passes the carrier water to line 18 and thence on the second valve stage 20 through which it passes to line 22. With the two valve stages so set, a continuous flow of carrier water is fed to the analytical train. Sample, which contains nitrate ions and interfering levels of chloride ions and bicarbonate ions (each in concentrations ranging from 1 to 500 mg/1), is continuously fed through line 24-24' to second valve stage 20 where it is directed to sample loop 26.

If sulfate ion is also present in the sample solution, there are two ways to perform the nitrate analysis and allow for sulfate presence. One way is to remove sulfate first by precipitation with a barium chloride solution and filtration to removes the barium sulfate. Means for carrying out such a step are depicted generally as 25 in FIG. 1. A second way is to electronically compensate the output signal by subtracting conductivity due to sulfate. This second method to deal with the sulfate presence is not shown in FIG. 1.

Sample loop 26 has preset volume and in the configuration shown is constantly being refilled with the most current sample available. In the configuration shown, loop 26 connects to first valve stage 16 which directs it to waste line 28. The sample delivery valves are maintained in this position until a steady state exists in the remainder of the analytical train.

Then the two stages of the control valve are moved (rotated) into their second position represented by dashed lines. This causes the carrier water stream 12 to be connected to the sample loop 26 via the first valve stage 16 and to force the predetermined volume of sample contained within the sample loop 26 out through line 22 and injected into the carrier flow. While this is happening, the sample flow from line 24-24' is fed through second stage 20 of the control valve 14 through line 18 to the first valve stage 16 and thence to waste line 28. The injected sample moves in essentially plug flow through line 22 to a suppressor column 30. The stream which has been sampled flows through the first stage of the valve through the sample loop, then through the second stage of the valve, and then to waste.

The above-described method of pumping eluant and injecting sample solutions into an analytical scheme is akin to common practice in ion chromatography measurements.

The sample so injected makes its way through line 22 to column 30, then through line 32 to column 34. These two columns contain ion exchange resins and are designed to removes or substantially reduce contaminating levels of chloride ion and bicarbonate ion.

These columns contain cation exchange resin in the silver ion form and the hydrogen ion form. As the sample passes through the column, bicarbonate ion is destroyed by reaction with hydrogen ion provided from the hydrogen ion form of the resin. The non-conducting compound $H_2CO_3$ is formed. Thus, no conductivity due to bicarbonate ion is available to be registered when the conductivity of the sample is measured by the detector.

The chloride ion in the sample in some manner reacts with the silver ion present in the silver form resin to retard its movement through the column. Although not understood with certainty, it is considered that the pattern which the chloride ion exhibits as it is held up and then gradually released by the silver resin cannot be predicted on the basis of ion-exchange theory. A possible mechanism of its passage is as follows:

As soon as chloride ion enters the column it reacts with the silver ion held on the resin to form solid silver chloride. As silver chloride has very limited solubility in the eluant, some of the chloride ion escapes through the column in a very low concentration in an undetected amount.

As eluant continues to flow through the column, it slowly dissolves the silver chloride precipitate and removes it from the column. This prevents a high back-pressure from developing during repeated analyses. It is not likely that silver chloride is completely removed from the column. If silver chloride is not completely removed from the column before more chloride is injected in a fresh sample, the incoming chloride will equilibrate with the unremoved silver chloride, driving the aqueous silver and some of the new aqueous chloride into the solid silver chloride form. In other words, the presence of added chloride suppresses the formation of aqueous silver chloride and slows the movement of the silver through the column. The new chloride wave will also react with the resin silver forming more silver chloride. The processes will continue as the sample solution and eluant pass through the column. The net result is a slow passage of chloride ions through the column.

The nitrate ion reacts with neither the hydrogen ion nor the silver ion and, thus, passes through the resin faster than the chloride ion.

Figure 2:
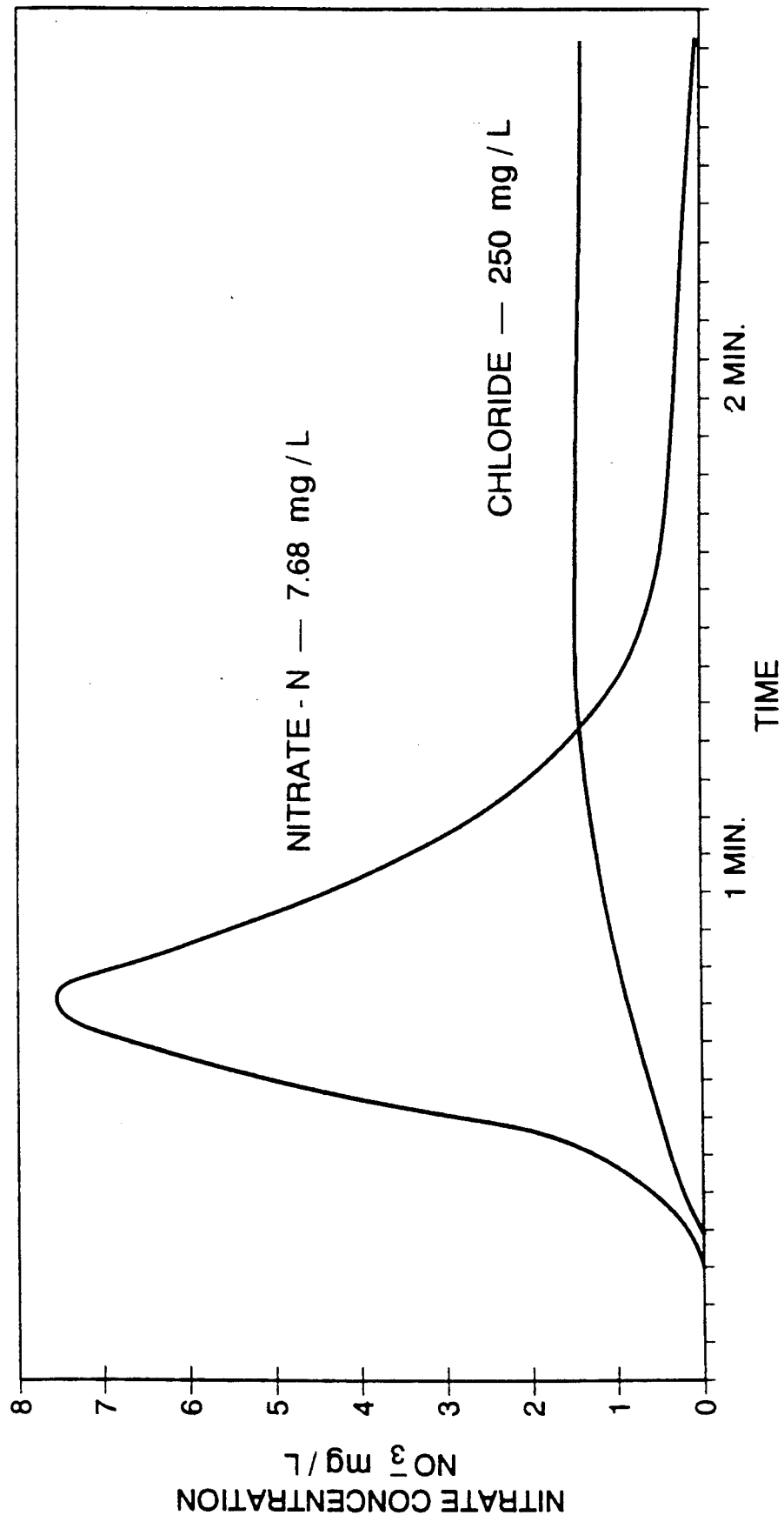

The sample is passed through the two suppressor separator columns and exits via line 36 and is passed to conductivity cell 38. Cell 38 is a conventional conductivity cell operated in a conventional mode. As the ions of the sample are slowly pumped through the column at a constant rate of flow, the conductivity rises and falls in accordance with the characteristics of the two different ions. FIG. 2 is a graph of conductivity as a function of time which results in a typical measurement. Nitrate ion emerges first in a wave of increased conductivity followed rapidly by a drop in conductivity. After the nitrate peaks, the chloride ion conductivity is registered as a slowly rising, very broad peak. These two different peaks are clearly shown in FIG. 2. The differences in the characteristics of the two peaks are the shape of the curves and the time of occurrence of the peaks. These differences are sufficient to allow the measurement of nitrate in the sample and distinguish it from the chloride. Typically, the sample residence time in the conductivity cell is from about 0.1 minute to about 100 minutes, depending upon the frequency of analyses. More preferred residence or cycle times are from about 0.5 to about 100 minutes.

The conductivity values so measured can be used as noted but more typically are converted to nitrate concentration values. This has been done in FIG. 2 where it can be seen that the conductivity values noted have been converted into nitrate concentration values. This can be done by running standards and from the results obtained with the standards providing a suitable conversion factor to go from conductivity values to nitrate concentration values.

In the version of the device shown above, the two suppressor columns are shown as two separate units. It will be appreciated that the order of these two columns is not critical and that the two different resins may be presented in a single column either with separate beds of each resin or by a mixture of the two resins in a single bed.

If sulfate ion is present in the sample, the sulfate ion will pass through the column with the nitrate ion. A sulfate wave will occur in the output of the conductivity meter superimposed on the nitrate wave. The output voltage from the conductivity meter will be the sum (or total), $C_T$, of the nitrate conductivity, $C_N$, and a sulfate conductivity, $C_S$. In order to correct for the sulfate wave interference, a second sample of the test water must be treated with a barium chloride or barium carbonate to precipitate the sulfate. This can be carried out at 25, if desired. This prepared sample can then be injected into the above apparatus to obtain the nitrate reading, $C_N$. The sulfate conductivity is determined by the difference between the two different conductivity readings, $C_S = C_T - C_N$. If all subsequent samples are untreated for sulfate removal and if all are from the same source in which the sulfate conductivity, $C_S$, remains constant, then the nitrate conductivity, $C_N$, is $C_T - C_S$ in the subsequent samples and may be determined directly by making the appropriate correction for $C_S$.

The analytical system of this invention has numerous advantages which lend it to broad application in water-treatment process control. For one, the system can be easily automated, with a timer controlling the sample injection to a desired period. The system uses only demineralized water as the eluant. The system generates an electrical signal which can be easily recorded, visualized and transmitted. Moreover, the reactions all occur without the consumption of large quantities of sample and costly reagents and the like which need to be periodically replenished. The process is not sensitive to pressure and can operated at any pressure in the range of 5 to 250 psig, if desired, making it easily adapted and applied to a wide range of water flows.

While this invention has been described with special reference being made to a preferred embodiment, it will be appreciated that the various embodiments can be altered without departing from the spirit of this invention which is defined by the following claims.

What is claimed is:

1. A method for determining the concentration of nitrate ions in aqueous effluent, the effluent additionally containing chloride ions and bicarbonate ions, which method comprises
   (1) admitting a measured volume of a sample of the effluent to a suppressor column, the suppressor column including ion-exchange columns containing silver ions and hydrogen ions in sufficient quantity to react with the bicarbonate and chloride ions and removes them from the sample, thereby forming a chloride ion- and bicarbonate ion-free sample
   (2) passing the chloride ion- and bicarbonate ion-free sample into a conductivity cell,
   (3) measuring the conductivity of the chloride ion- and bicarbonate ion-free sample, and
   (4) relating the conductivity so measured to the concentration of nitrate ion in the sample.

2. The method of claim 1 wherein in step (3) the measuring of conductivity of the chloride ion and bicarbonate ion free sample is carried out in a time period of from about 0.1 minute to about 100 minutes.

3. The method of claim 2 wherein the time period is from about 0.5 minutes to about 100 minutes.

* * * * *